United States Patent [19]
Bar-Cohen et al.

[11] Patent Number: 6,092,421
[45] Date of Patent: Jul. 25, 2000

[54] ULTRASONIC SYSTEM FOR AUTOMATIC DETERMINATION OF MATERIAL STIFFNESS CONSTANTS

[75] Inventors: Yoseph Bar-Cohen, Seal Beach; Shyh-Shiuh Lih, Chatsworth, both of Calif.

[73] Assignee: California Institute of Technology, Pasadena, Calif.

[21] Appl. No.: 09/188,703

[22] Filed: Aug. 28, 1998

Related U.S. Application Data

[60] Provisional application No. 60/057,403, Aug. 29, 1997.

[51] Int. Cl.$^7$ .................................................. G01N 29/04
[52] U.S. Cl. .................................. 73/624; 73/621; 73/627
[58] Field of Search .............................. 73/621, 620, 619, 73/618, 627, 634, 633, 632, 588, 584, 159, 624

[56] References Cited

U.S. PATENT DOCUMENTS

| | | | |
|---|---|---|---|
| H924 | 6/1991 | Chimenti | 73/644 |
| 4,674,334 | 6/1987 | Chimenti et al. | 73/627 |
| 4,825,423 | 4/1989 | Yamanaka | 367/99 |
| 4,976,150 | 12/1990 | Deka | 73/644 |

*Primary Examiner*—Richard A. Moller
*Attorney, Agent, or Firm*—Fish & Richardson P.C.

[57] ABSTRACT

A system which rapidly determines the elastic stiffness constants of materials in plate shape as well as characterize material flaws that are affecting these constants. Rapid (below a minute) nondestructive evaluation system allow for the determination of material stiffness constants, low noise data acquisition algorithm for measuring spectral data. A real time method of displaying leaky Lamb wave spectral data.

16 Claims, 6 Drawing Sheets

ULTRASONIC SYSTEM FOR AUTOMATIC DETERMINATION OF MATERIAL STIFFNESS CONSTANTS

This application claims benefit of Provisional Application Ser. No. 60/057,403 filed Aug. 29, 1997.

BACKGROUND

Composite materials are increasingly being applied to aircraft, spacecraft, large space precision optics and various structural components. Reliable quantitative inspection methods can be used to determine the integrity and serviceability of composite structures. The elastic stiffness constants of composites are key contributors to the mechanical behavior and dimensional stability of the related structures. It is therefore important to determine these characteristics accurately.

Destructive tests are often used to determine the elastic properties of the material. These tests are expensive and can only be performed on representative samples, since the samples are eventually destroyed. On the other hand, nondestructive evaluation methods could be used to test each structure itself, rather than only testing a representative sample. Nondestructive evaluation can also be used to determine the status of an aging structure without removing it from service.

Attempts at nondestructive evaluation for material characterization of composites has so far met with limited success. The conventional pulse-echo and through-transmission tests are capable of yielding only one of the five stiffness constants of composites (transversely isotropic material behavior).

The leaky Lamb wave (LLW) technique, pioneered by an inventor of this system, Yoseph Bar-Cohen, uses guided waves which propagate in parallel to the surface of the laminate. This has been shown to yield all the matrix-dominated constants. These constants are indicative of the quality of the material once the correct fibers are chosen. Currently, there is no practical nondestructive method of measuring the matrix-dominated properties. The existing leaky Lamb wave (LLW) test capability has also been slow, e.g. requiring about half an hour for each point.

The LLW data acquisition process involves the acquisition of the reflected wave spectra at various angles of incidence. The amplitude is measured individually for signals in a preselected frequency range. Once this stage is complete, the minima, representing the plate wave modes, that appear on the reflected spectra for each given angle of incidence, are identified. These modes are recorded for the specific angle of incidence and converted to a phase velocity using Snell's law. The process of mode determination is continued for the range of incidence angles that is usually from 12.5° to 50° for graphite/epoxy composite material but may be different for other materials. The curve that is produced is known as the characteristic dispersion curve.

The dispersion curve represents the plate wave modes for the given direction with the fibers. It is useful to measure the dispersion curves for the 0°, 45° and 90° polar angles, measured with the first layer of the laminate, as a means of characterizing the laminate.

Once the dispersion data is available, an inversion technique is applied to determine the elastic stiffness constants. The method of inversion, is known in the art and described in Y. Bar-Cohen, A. K. Mal and S. -S. Lih, "NDE of Composite Materials Using Ultrasonic Oblique Insonification," *Materials Evaluation*, Vol. 51, No. 11, (November 1993) 1285–1296). It has allowed determination of the properties based on single layer data.

Another limitation occurs when testing multi-layered composites because of the large number of associated variables including each layer thickness, density and the presence of a rich epoxy layer at the interfaces.

Setup of the LLW scanner and its control is also complex and requires highly skilled operators. The data acquisition is slow for practical use—about 30 minutes per point. The inversion algorithm has been complex and required the characterization of many variables that are associated with the individual layers of composites.

Thus, while the LLW technique is known, basic problems with the existing capability have restricted its practical application.

SUMMARY

The present specification discloses a technique that allows making measurements at quasi real-time performance using a new automated technique. The slow rate of the data acquisition portion of the process has been one of the bottlenecks to the application of LLW as a nondestructive evaluation technique. The inventors found that the need to take the data one frequency at a time has reduced the speed. This system addresses those problems.

BRIEF DESCRIPTION OF THE DRAWINGS

These and other aspects of the invention will be described with reference to the accompanying drawings, in which.

DESCRIPTION OF THE PREFERRED EMBODIMENTS

Figure 1:
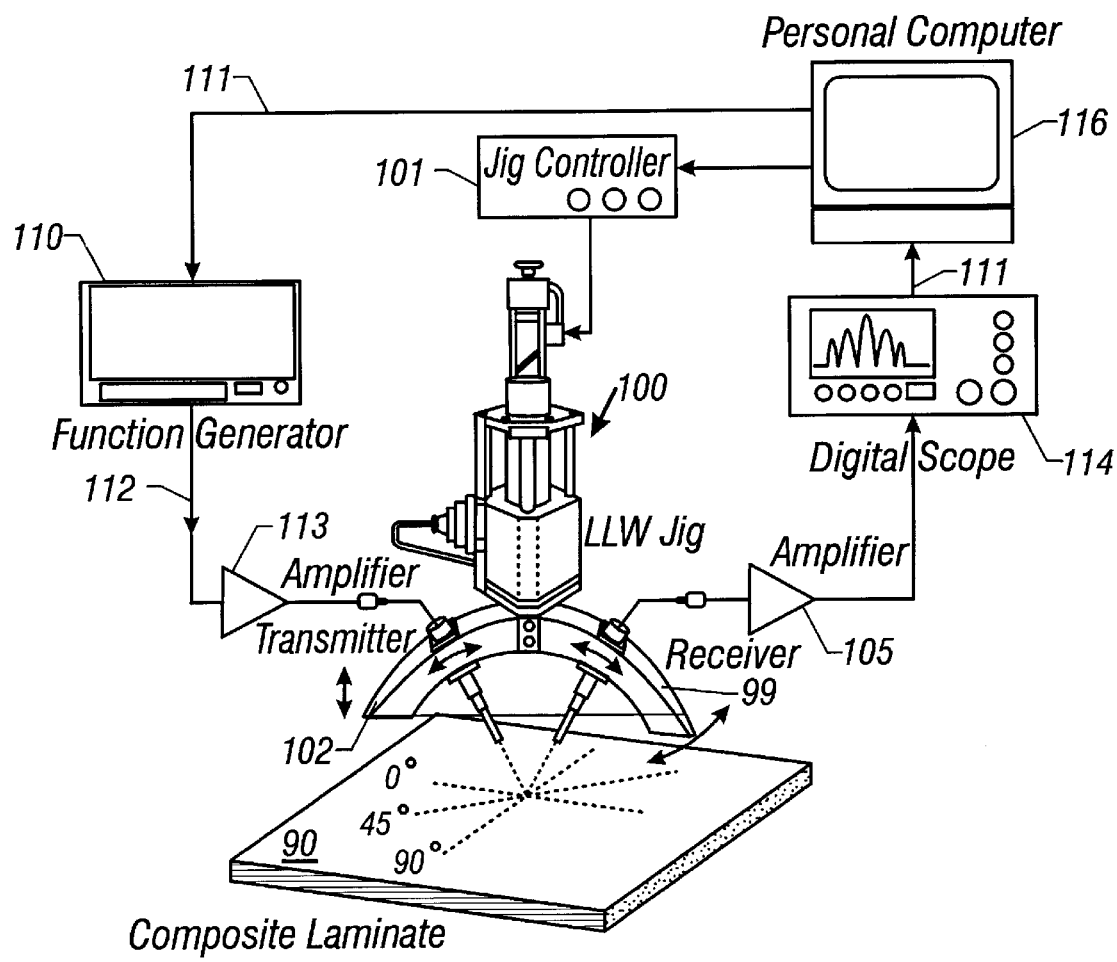
FIG. 1 shows a schematic view of the system.

The embodiment uses a function generator 110 to produce the drive 112 to the transducer transmitter 102. The output 112 of function generator 110 is amplified by amplifier 113 and coupled to transmitter 102. Transmitter 102 emits the beam to material 90, and the beam is reflected and received by receiver 104. The received output is amplified by amplifier 105 and coupled to scope 114 for display. A substantially arcuate shaped holder couples the transmitter and receiver 104 to one another.

Digital scope 114 acquires the responsive communication and couples that response to a personal computer 116 via IEEE-488 parallel interface as shown as 111.

The function generator 110 is used to produce a FM modulated sweep operation. Signals are transmitted that include sequentially-varying frequency tone-bursts. The received signal represents spectral data in the time domain which can be directly displayed on any scope without Fourier analysis. The received reflection spectrum has low frequency characteristics. Therefore, high frequency noise, which might otherwise interfere with the measured spectrum, is filtered by filter 107 to reduce noise. The filtered signals are amplified by amplifier 105.

The LLW scanner 100, including transmitter 102 and receiver 104, is controlled by control hardware 101. The control system controls the height, rotation angle and the angle of incidence of transducer assembly 99. A control system of the computer automatically sets the height of the transducer pair—transmitter 102 and receiver 104—by finding the optimum position where the receiver 104 is placed at the null zone of the leaky Lamb waves.

This is done by treating the acquired reflected spectrum as a statistical distribution function. The computer automatically determines the proper height by varying the height and finding an optimum height where maximum consecutive standard deviation is obtained.

This compares with the prior art systems where the height is searched manually by the operator who visually identifies the location at which the highest peak amplitude is observed with the lowest minima of the LLW modes. This requires substantial skill and training. As a result, the existing approach was not user friendly and led to data inconsistency caused by operator error.

Figure 2:
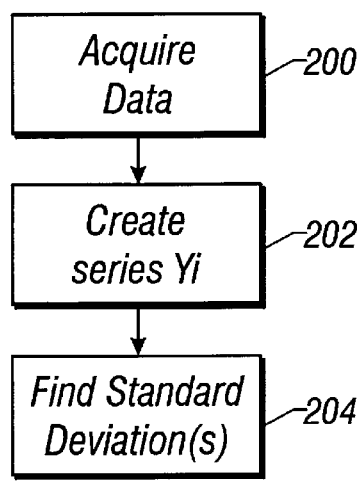
FIG. 2 shows a flowchart of operation.

The procedure for the automatic height adjustment technique is described with reference to the flowchart of FIG. 2.

Assume that there is a total set of n raw data, $x_1$ to $x_n$, representing the amplitudes of a signal in the frequency domain. This data is acquired at step 200. Since the contrast between the minima and the adjacent points is important, a series $y_i=(x_{i+1}-x_i)$, i=1 to n−1 is created at step 202. The standard deviation of this new series is used as an indication for adjustment of the transducer height. The location at which the maximum standard deviation, s, is obtained is derived as follows, $$s = \sqrt{\frac{\sum_{i=1}^{n-1}(y_i - \bar{y})^2}{n-2}}$$

where $\bar{y}$ is the mean value of the series $y_i$, i=1 to n−1. Considering that the series $x_i$ starts and ends both at zero, the mean value of the series $y_i=(x_{i+1}-x_i)$, i=1 to n−1, must be zero. So the standard deviation becomes, $$s = \sqrt{\frac{\sum_{i=1}^{n-1} y_i^2}{n-2}} = \sqrt{\frac{\sum_{i=1}^{n-1}(x_{i+1}-x_i)^2}{n-2}}$$

$$= \sqrt{\frac{\sum_{i=1}^{n-1}(x_{i+1}^2 - 2x_{i+1}x_i + x_i^2)}{n-2}}$$

$$= \sqrt{\frac{2\sum_{i=1}^{n-1} x_i^2 - 2\sum_{i=1}^{n-1}(x_{i+1}x_i)}{n-2}}$$

s values are recorded and the maximum is searched while the height of the LLW setup is changed up and down around the expected value.

Figure 3:
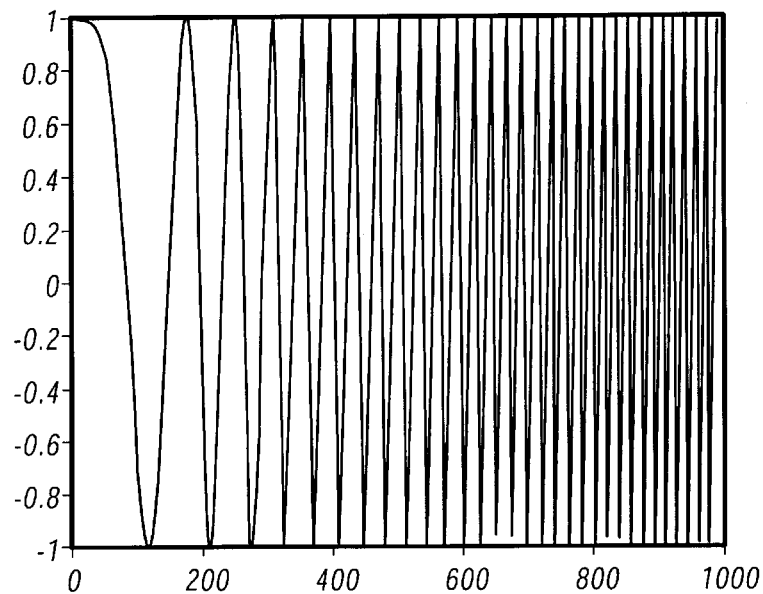
FIG. 3 shows an FM modulated insonification signal.

The control of the incidence angle allows simultaneously changing of the transmitter and receiver angle while maintaining a pivot point on the part surface and assuring accurate measurement of the reflected ultrasonic signals. The FM function is expressed as $$FRQ=STA \times (1+K)^N$$

where FRQ is the frequency value, STA is the starting frequency of the frequency-sweep signal, K and N are functions of the sweep time. The preferred setup uses the values K=0.015625 and N=149. The start and stop frequency of the frequency-sweep signal is 1 MHz and 10 MHz, respectively. This generator also provides a reference frequency marker for the calibration of the data acquisition when converting the scale of the signal x-axis from time to frequency domain as shown in FIG. 3.

The preferred embodiment uses digital scope 114 to acquire the reflection spectral data after it is amplified and filtered. To produce an integrated system with faster operation, this data acquisition can be miniaturized and compacted to reside on a single electronic board of a personal computer. Originally, the acquisition of the LLW modes was a single tone-burst frequency at a time at each angle of incidence. This step is eliminated in this system. The program controls the LLW scanner to start it from the home position at which the transducers are at known coordinates, e.g. the origin (0,0).

Figure 4:
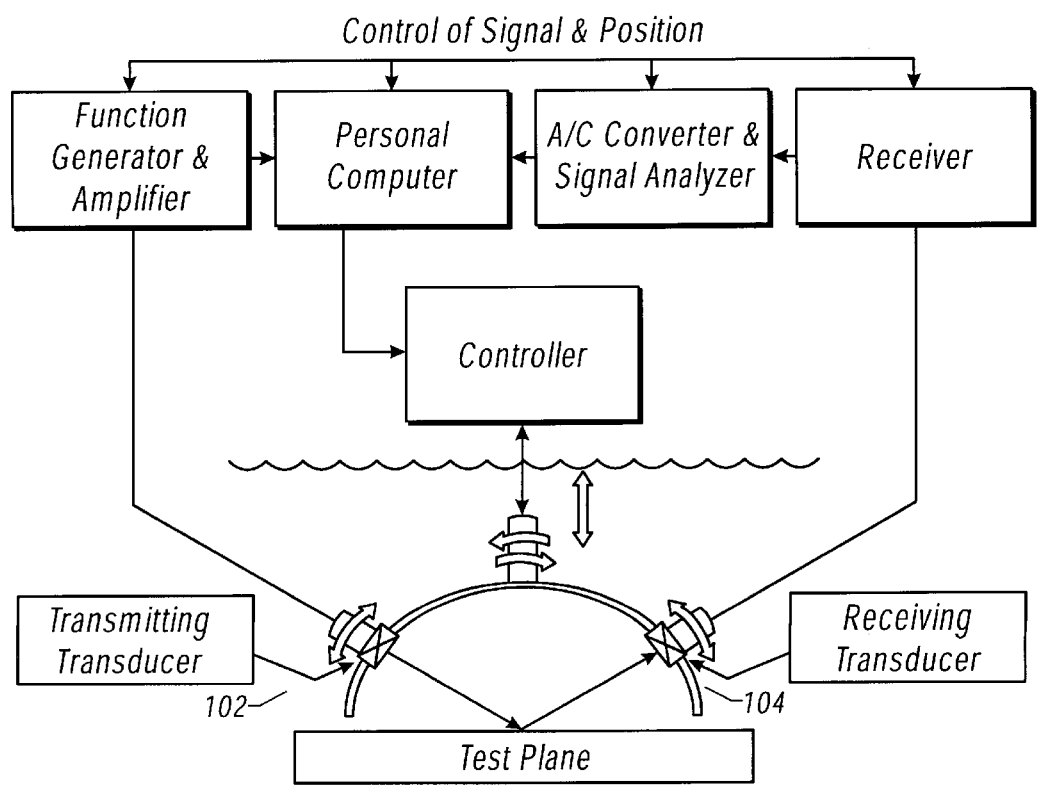
FIG. 4 shows a schematic diagram of the data acquisition system.

The data acquisition block diagram is shown in FIG. 4. The signals that are induced by the transmitter are shown being received, processed and analyzed by a personal computer after being digitized.

A user selectable menu provides an improved user allowing the selection of the desired test options. These options include setting up the system as well as preparing it for data acquisition and later performing the inversion analysis.

Figure 5:
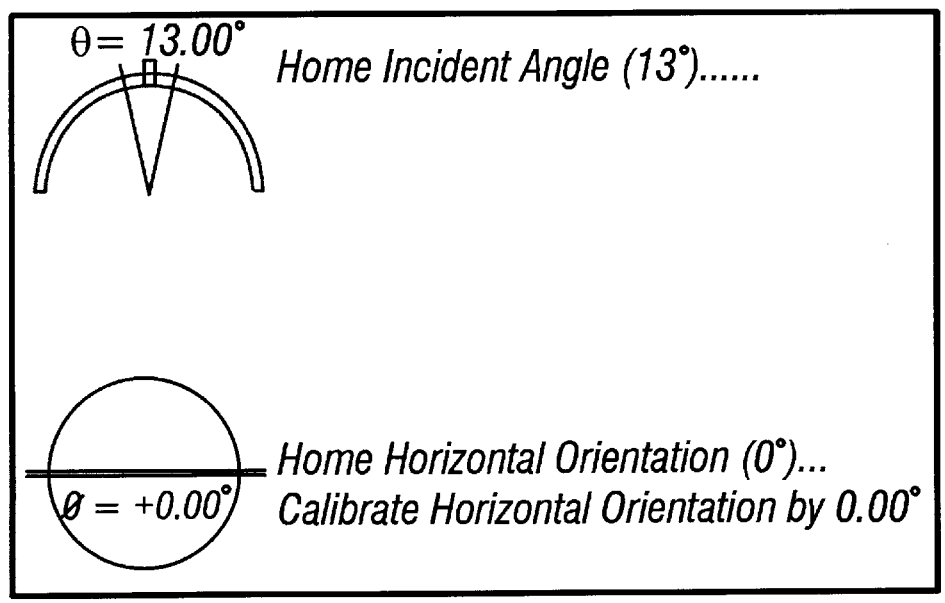
FIG. 5 shows a view of the computer display at the stage of system homing.

The processor begins by setting the LLW scanner at its home position. This includes placing the receivers at 12.5° and the scanner plan along the fibers of the composite laminate. The system moves the probes and the fixture in a sequence of travel that allows finding the location of the limit switches where the motion stops. That location is identified as a home coordinate. The home positioning is important since it allows the system to operate without an encoder in an open loop mode and it is essential to find the home to determine the location of the transducers during the data acquisition process. The operator receives a computer display feedback of this operation as shown in FIG. 5.

Figure 6:
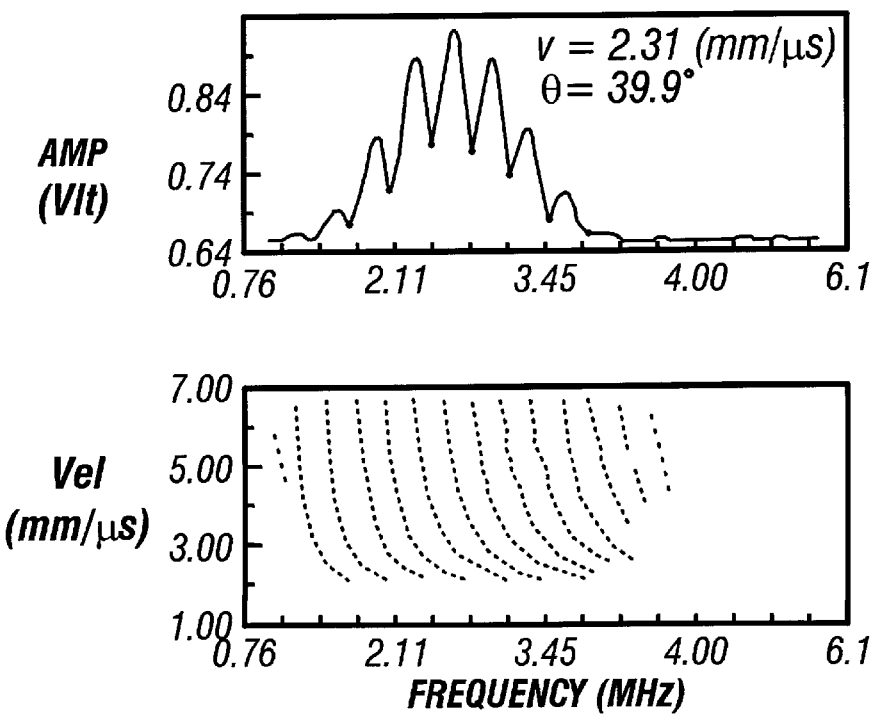
FIG. 6 shows a view of the acquired data for a given angle of incidence (39.9°) during the acquisition of the dispersion curve, where the top section shows the reflection spectrum, the computer marks the minima associated with the plate wave modes and the bottom shows the accumulating data on the dispersion curve.
Figure 7:
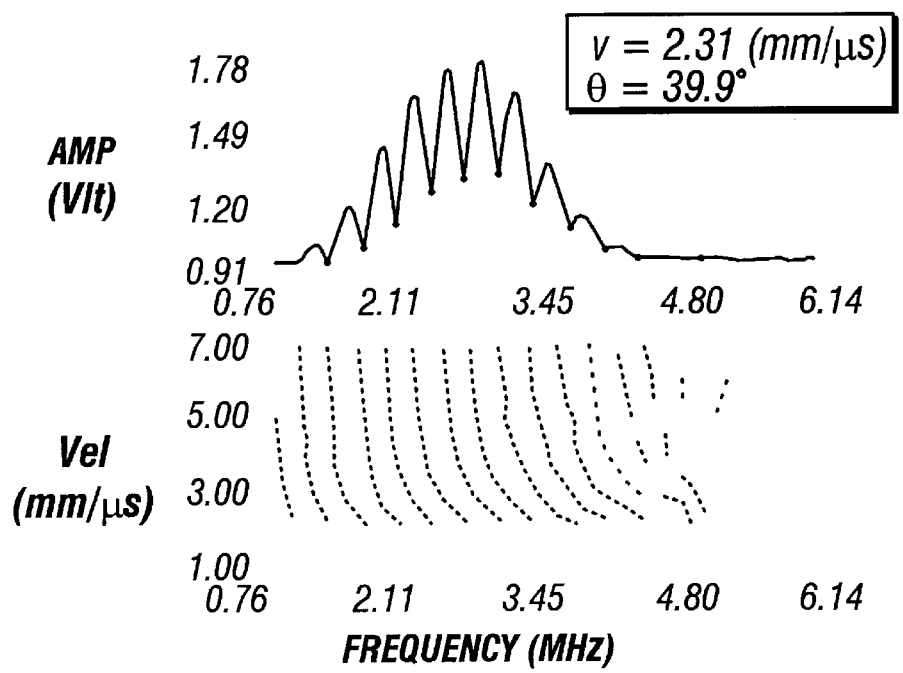
FIG. 7 shows a view of the screen after the completion of the data acquisition phase and the data inversion. The elastic stiffness constants are inverted from the dispersion curve and are presented as a list on the left.

Once this stage is complete, the computer starts the data acquisition process. At each of the selected angles of incidence, the reflection spectrum is acquired and the location of the minima (LLW modes) is identified and marked on the reflection spectrum. These minima are accumulated on the dispersion curve, which is shown on the lower part of the display as shown in FIG. 6. The inventor's experiments have shown that the process of acquiring a dispersion curve for 20 different angles of incidence takes less than 45 seconds. This is significantly faster that the current 15–30 minute process. Once the dispersion data is ready, the inversion option of the software is activated and the elastic stiffness constants are determined and presented on the display as shown in FIG. 7. The inversion is an analytical process which seeks the stiffness constants which form a best fit between the measurements and the analytical predictions.

To enhance the accuracy of the inversion of the material stiffness constants, dispersion curves can be acquired in the form of a detailed image. The image x-axis shows the frequency, the y-axis shows the phase velocity and each of the pixels of the image has a color or a shade of gray that represents the amplitude of the reflection spectrum at the given phase velocity (i.e., angle of incidence). A color or shades of gray scale lookup table on the computer monitor allows the user to view the level of the reflection amplitude at the given frequency and phase velocity.

Figure 8:
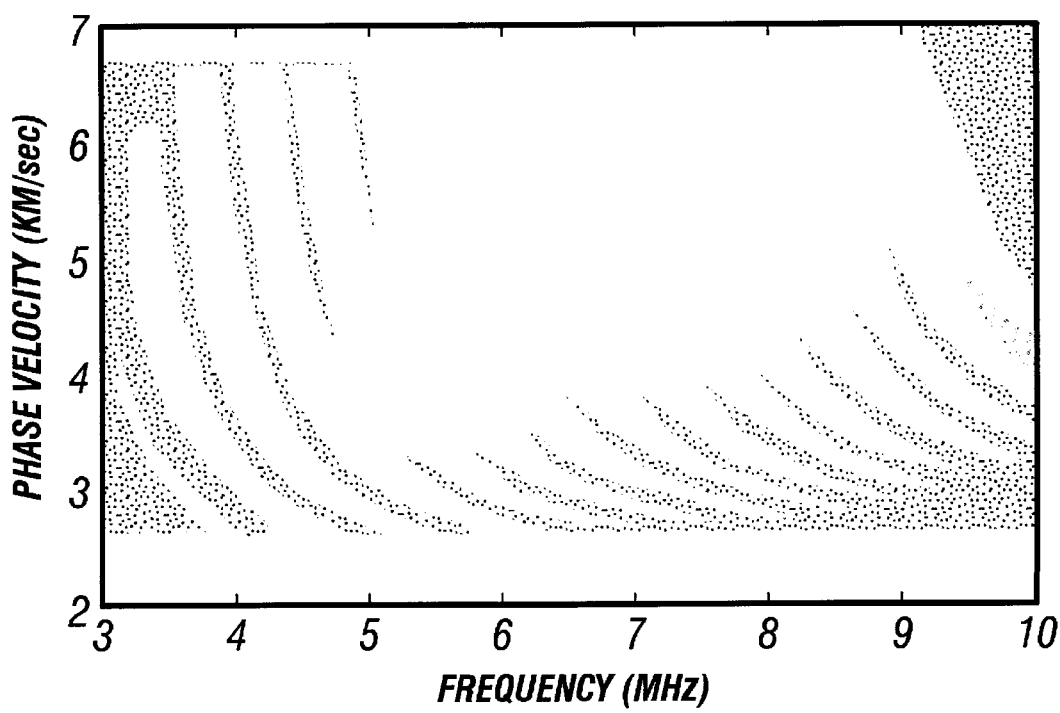
FIG. 8 shows a view of the imaging method of presenting a dispersion curve.

An example of a dispersion curve image of a unidirectional 24 layer thick laminate tested along the fibers is shown in FIG. 8. This method allows viewing LLW modes that are far into the amplitude range which has a very low signal to noise ratio. The white curved lines show the modes on the background of the reflected spectra.

Figure 9A:
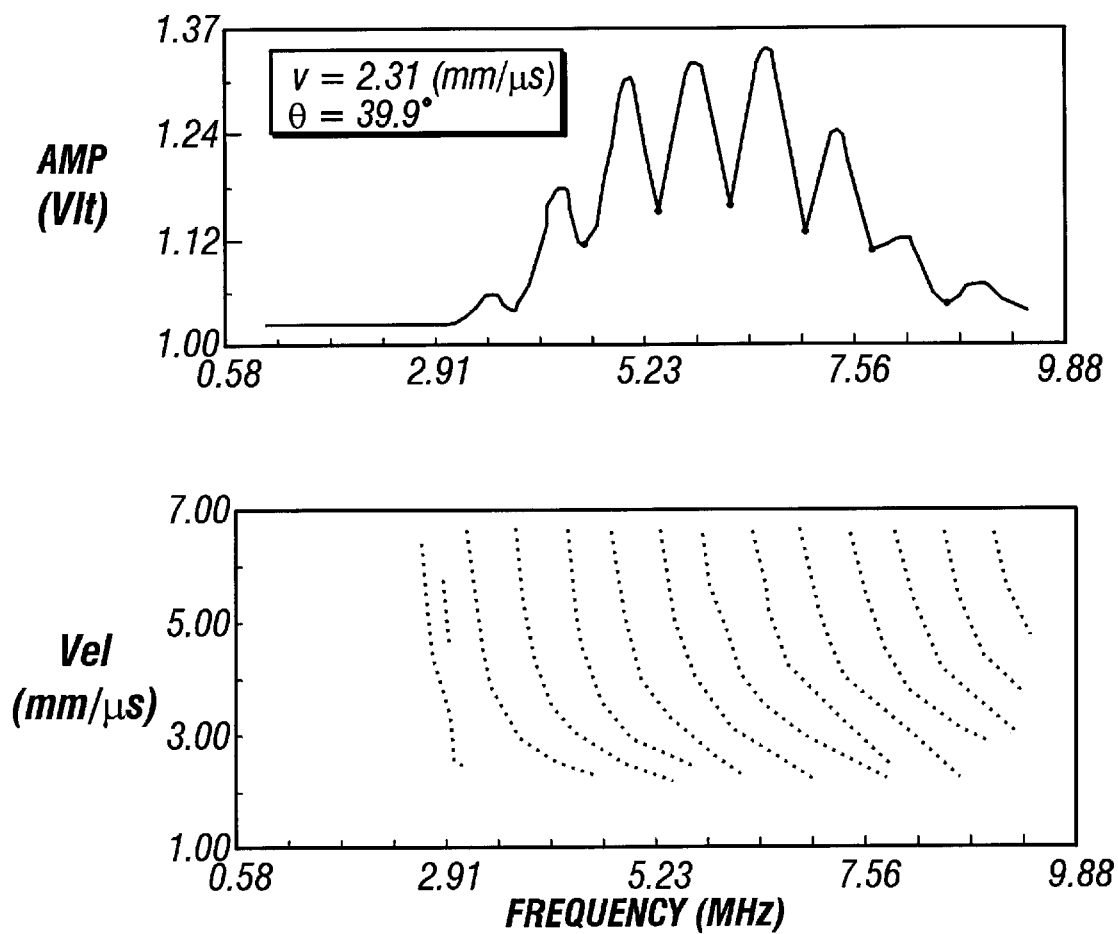
FIGS. 9A and 9B show reflection curves for a specific laminate.
Figure 9B:
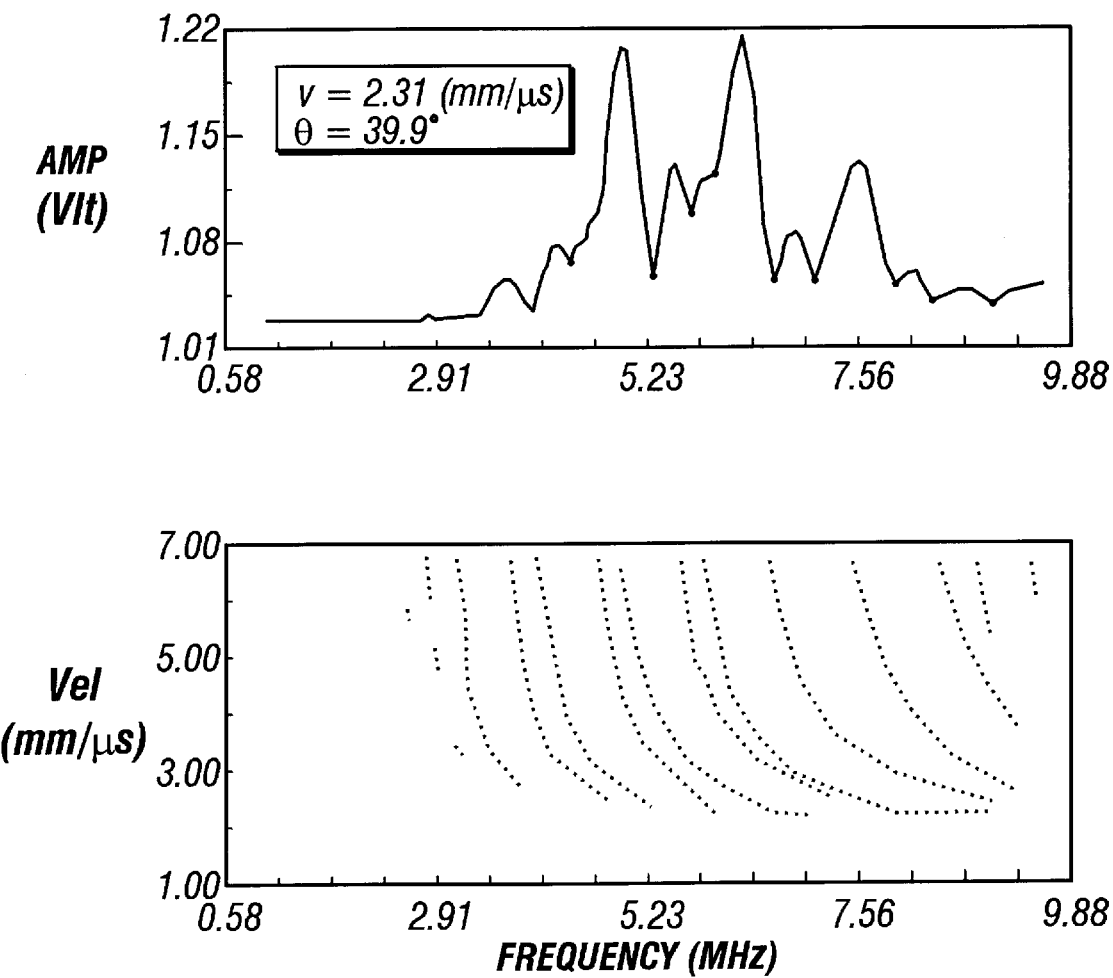

Using the RMSCD system, various defects can be detected and characterized based on the signature and quantitative data that is available from the dispersion curves. In FIG. 9a, the response from a defect-free graphite/epoxy laminate tested at the 0° polar angle is shown. In FIG. 9b, the response from an area with a layer of simulated porosity (microballoons) is presented. At frequencies above ~5 MHz the reflection spectrum from the porosity emulates a delamination and modifies the dispersion curve to appear the same as half the thickness laminate.

The disclosed system is applicable to both metals and composite materials.

What is claimed is:

1. A material processing device, comprising:
    a transmitter which produces a first wave and a receiver which receives a reflection of the first wave from a material to be tested, said first wave being one whose characteristics can be used to determine information about the material to be tested;
    a holder, having surfaces holding said transmitter and said receiver and operable to control at least a height and orientation angles of said transmitter and receiver relative to the material to be tested; and
    a computing device, coupled to said receiver, for finding an optimum position for said holder and said transmitter and receiver based on said reflection, said computing device operable to obtain a reflected spectrum and to determine maximum consecutive standard deviations as a statistical distribution function from the reflected spectrum so as to find an optimum height from said standard deviations.

2. A device as in claim 1, wherein said transmitter is configured so that said first wave causes leaky Lamb waves in the material to be tested, and said computing device finds an optimum position where the receiver is placed at a null zone of the leaky Lamb waves.

3. A device as in claim 1, further comprising a filter, which filters high frequency noise from the reflected spectrum.

4. A device as in claim 1, wherein said transmitter is configured in a way that the acoustic frequency of the first wave is a function of time to produce different modes of Leaky Lamb wave modes in the material.

5. A device as in claim 1, wherein said computing device is configured to produce a graphic representation of the reflected spectrum.

6. A method of operating a Leaky Lamb wave transducer, comprising:
    moving the transducer in a sequence of travel that allows finding a limit location with respect to a material under measurement;
    establishing said limit location as a home location;
    operating the transducer in an open loop mode, without a position encoder, based on moving the transducer relative to said limit location to produce an incident acoustic wave to the material; and
    positioning a receiver relative to the transducer and the material to obtain a reflected spectrum from a reflection of the incident acoustic wave from the material and to determine maximum consecutive standard deviations as a statistical distribution function from the reflected spectrum so as to find an optimum height of the transducer from the material according to said standard deviations.

7. A method as in claim 6, wherein said operating comprises moving the transducer to a plurality of selected angles of incidence relative to a material to be tested.

8. A method as in claim 7, further comprising acquiring a reflection spectrum at each of said selected angles of incidence, and automatically detecting a location of the minima of modes of Leaky Lamb waves in each reflection spectrum.

9. A method as in claim 8, further comprising matching said minima to a best fit of composite parameters, and outputting said parameters.

10. A method as in claim 6, further comprising processing the reflected spectrum obtained at difference angles of incidence to form a dispersion curve to represent phase velocities of Leaky Lamb waves in the material for different angles of incidence and inverting said dispersion curve to obtain parameters.

11. A method of operating a Leaky Lamb wave system, comprising:
    using a transmitter to transmit waves towards a material which produces reflected waves that are received by a receiver;
    obtaining a reflected spectrum from the reflected waves;
    processing the reflected spectrum to determine an optimum height of the transmitter and the receiver relative to the material where the receiver is placed at null zone of the Leaky Lamb waves according to a standard deviation in the measured magnitudes of the reflected waves for different heights of the transmitter and receiver relative to the material; and
    automatically setting a height of the transmitter and receiver at the optimum height.

12. A method of using acoustic waves to probe characteristics of a material, comprising:
    positioning a transmitter to transmit an acoustic wave to a material, the acoustic wave operable to generate Leaky Lamb waves in the material;
    positioning a receiver relative to said transmitter and the material to receive a reflected acoustic wave from the material;
    varying positions of the transmitter and the receiver with respect to the material to measure magnitudes of the reflected acoustic wave at different positions;
    computing standard deviations of the magnitudes of the reflected acoustic waves so that the standard deviation is maximum at the optimum positions of the transmitter and receiver;
    selecting optimum positions of the transmitter and the receiver relative to the material based on the maximum standard deviations of the reflected acoustic waves at different positions;
    measuring the reflected acoustic wave when the transmitter and the receiver are at the optimum positions to obtain a reflected spectrum; and
    processing the reflected spectrum to determine at least one parameter of the material.

13. A method as in claim 12, wherein the acoustic wave from the transmitter has a frequency that changes with time.

14. A method as in claim 12, further comprising providing a control system to automatically position the transmitter and the receiver relative to the material at the optimum positions.

15. A method as in claim 12, further comprising processing the reflected spectrum to produce a graphic representation to allow a user to visually identify noise data in the reflected spectrum.

16. A method as in claim 12, wherein the material parameter includes an elastic constant of the material.

* * * * *

UNITED STATES PATENT AND TRADEMARK OFFICE
CERTIFICATE OF CORRECTION

PATENT NO.    : 6,092,421
DATED         : July 25, 2000
INVENTOR(S)   : Shyh-Shiuh Lih and Yoseph Bar-Cohen It is certified that error appears in the above-identified patent and that said Letters Patent is hereby corrected as shown below:

Column 1,
Line 7, before BACKGROUND, insert the following,
-- STATEMENT AS TO FEDERALLY-SPONSORED RESEARCH
U.S. Government may have certain rights in this invention pursuant to Nasa contract number NAS7-1407. --

Signed and Sealed this

Tenth Day of May, 2005

JON W. DUDAS
*Director of the United States Patent and Trademark Office*